United States Patent
Gnanaprakasam et al.

(10) Patent No.: US 7,417,143 B2
(45) Date of Patent: Aug. 26, 2008

(54) PROCESS FOR THE PREPARATION OF TAZOBACTAM IN PURE FORM

(75) Inventors: Andrew Gnanaprakasam, Chennai (IN); Udayampalayam Palanisamy Senthilkumar, Erode dist (IN); Gaddam Om Reddy, Chennai (IN)

(73) Assignee: Orchid Chemicals & Pharmaceuticals Limited, Chennai (IN)

( * ) Notice: Subject to any disclaimer, the term of this patent is extended or adjusted under 35 U.S.C. 154(b) by 507 days.

(21) Appl. No.: 11/098,526

(22) Filed: Apr. 5, 2005

(65) Prior Publication Data
US 2005/0228176 A1 Oct. 13, 2005

(30) Foreign Application Priority Data
Apr. 7, 2004 (IN) .................... 319/CHE/2004

(51) Int. Cl.
*C07D 499/18* (2006.01)
(52) U.S. Cl. ..................................... 540/310
(58) Field of Classification Search ............. 540/310
See application file for complete search history.

(56) References Cited

U.S. PATENT DOCUMENTS 4,626,384 A * 12/1986 Tanaka et al. .............. 540/306
2002/0193587 A1* 12/2002 Shimabayashi et al. ..... 540/314
2002/0193588 A1* 12/2002 Shimabayashi et al. ..... 540/314
2003/0232983 A1* 12/2003 Deshpande et al. ......... 540/346
2004/0162277 A1* 8/2004 Shimbayashi et al. ....... 514/192

FOREIGN PATENT DOCUMENTS

JP A-63-066187 3/1988

* cited by examiner

*Primary Examiner*—Mark L Berch
(74) *Attorney, Agent, or Firm*—Oliff & Berridge, PLC

(57) ABSTRACT

An improved process for the purification of tazobactam or its derivatives of the formula (I)

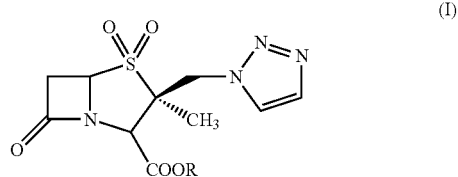

(I)

wherein R represents hydrogen, $C_1$-$C_6$alkyl, p-methoxybenzyl, o-nitrobenzyl, p-nitrobenzyl, o-chlorobenzyl, benzyl or diphenylmethyl, which comprises the steps of:
  i) slurrying the compound of formula (I) containing the impurity of the formula (V) using a solvent in the presence or absence of tartaric acid with or without the presence of water at 20-50° C. and
  ii) isolating the compound of formula (I) in pure form.

2 Claims, No Drawings

PROCESS FOR THE PREPARATION OF TAZOBACTAM IN PURE FORM

FIELD OF THE INVENTION

The present invention relates to an improved process for the purification of Tazobactam or its derivatives of formula (I). More particularly the present invention relates to an improved process for the purification of Tazobactam or its derivatives with low content or free of isomeric impurity.

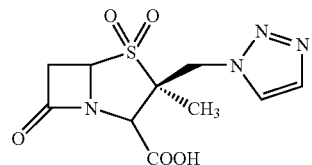
(I)

The present invention provides compound of formula (I) having less than 0.5% w/w isomeric impurity of formula (V).

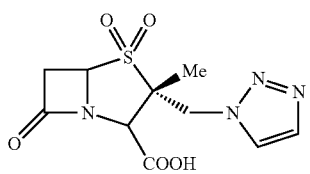
(V)

BACKGROUND OF THE INVENTION

Tazobactam is chemically known as 2α-methyl-2β-(1,2,3-triazol-1-yl)-methylpenam-3α-carboxylate-1,1-dioxide. It is an orally effective pencillin antibiotic having a broad spectrum of antibacterial activity against both gram positive and gram-negative organisms and is disclosed in U.S. Pat. No. 4,562,073.

U.S. Pat. No. 4,562,073 discloses tazobactam of formula (I) and its derivatives. This patent also describes process for their preparation as shown in scheme-1 below:

Scheme -I

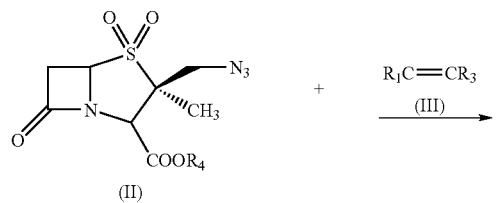

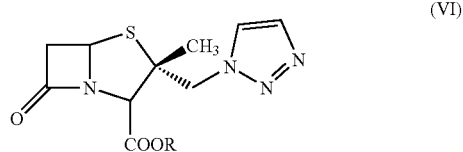

wherein $R_1$ is hydrogen or trialkylsilyl; $R_2$ is hydrogen, trialkylsilyl or $COOR_2'$, wherein $R_2'$ is hydrogen, $C_{1-18}$ alkyl, $C_{2-7}$ alkoxymethyl etc., $R_3$ has the same meaning as above $R_2$, and $R_4$ represents carboxyl protecting group.

Ogawa et.al Japan. Kokai Tokkyo Koho (1988), 8 pp; JP 63066187) reported the isomer impurity of tazobactam of the formula (V)

(V)

Tazobactam, containing the above isomeric impurity around 15-22%, needs to be purified to the level of <0.5%, more specifically <0.2% or <0.1%. The diastereomeric sulfide (VI), formed along with the sulfide of the formula (VII) (Tazobactam intermediate) during the condensation of the 3-halocepham of (VI)

-continued

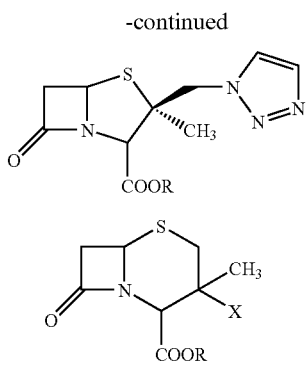

the formula (VIII) with 1,2,3-1H-triazole, gets converted to the corresponding isomeric impurity of the formula (V), by the subsequent oxidation followed by deprotection. As a result, Tazobactam isolated from the reaction mixture gets contaminated with the isomeric impurity, the removal of which has been found to be very difficult.

During our research efforts to produce pure tazobactam, we have investigated various methods to remove the isomeric impurity and found that this impurity can be removed at the last stage or at the penultimate stage with certain selected solvents and reagents.

In addition, we also found that tazobactam can be selectively crystallized from the solution containing the above impure tazobactam, if the crystallization is carried out in the presence of certain selected solvents.

OBJECTIVE OF THE INVENTION

The main objective of the present invention is to provide a process for the purification of Tazobactam or its derivatives.

Another objective of the present invention is to develop a simple and commercially viable purification process for the purification of tazobactam with low content or free of isomeric impurity.

Still another objective of the present invention is to develop a simple process for crystallizing pure tazobactam, with low content/free of isomeric impurity, directly from the reaction mixture.

Yet another objective of the present invention is to provide Tazobactam of formula (I) having less than 0.5% w/w of impurity of formula (V) specifically less than 0.1%.

SUMMARY OF THE INVENTION

Accordingly, the present invention provides an improved process for the purification of tazobactam or its derivatives of the formula (I) or preparation of tazobactam or its derivatives of the formula (I) having less than 0.5% w/w of impurity of formula (V)

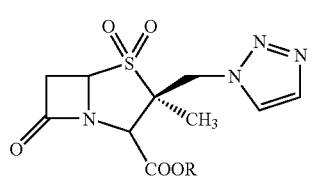

wherein R represents hydrogen, $C_1$-$C_6$alkyl, p-methoxybenzyl, o-nitrobenzyl, p-nitrobenzyl, o-chlorobenzyl, benzyl or diphenylmethyl, which comprises the steps of:
i) stirring the impure compound of formula (I) containing the impurity of the formula (V) with a solvent optionally in the presence of tartaric acid and water at 20-50° C. and
ii) isolating the compound of formula (I) in pure form.

In an alternate approach, the present invention also provides an improved process for crystallizing pure tazobactam of the formula (I) having less than 0.5% w/w of impurity of formula (V)

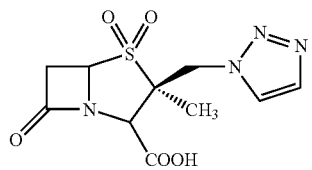

which comprises the steps of:
i) crystallizing out the pure tazobactam of formula (I), from the reaction mixture containing a mixture of tazobactam of the formula (I) and the isomeric impurity of the formula (V), in the presence of a solvent at −10 to 50° C. and
ii) isolating the compound of formula (I) in pure form.

The present invention also provides a compound of formula (I) having less than 0.5% w/w of impurity of formula (V).

DETAILED DESCRIPTION OF THE INVENTION

In an embodiment of the present invention the solvent used is selected from methyl ethyl ketone, acetic acid, formic acid, propionic acid, DMF, DMAC, DMSO, cyclohexanone, acetone, MEK and the like or mixtures thereof with small quantity of water.

In still another embodiment of the present invention the starting material of the present invention contains the isomeric impurity of formula (V) more than 0.5%.

In another embodiment of the present invention, the tartaric acid used is L-tartaric acid, D-tartaric acid or (±)-tartaric acid.

In still another embodiment of the present invention the Tazobactam of formula (I) is prepared by utilizing the processes known in the literature.

Thus compound of formula (I) or its salt having less than 0.5% w/w of impurity of formula (V) or more specifically less than 0.1% is formulated alone or in combination with piperacillin or its salt.

The foregoing technique has been found to be attractive from commercial, technological perspective.

Many other beneficial results can be obtained by applying disclosed invention in a different manner or by modifying the invention within the scope of disclosure.

The following examples are provided by way of illustration only and should not be limited to construe the scope of the invention.

EXAMPLE 1

Purification of Tazobactam Using Methyl Ethyl Ketone

Tazobactam (36.2 g) containing the isomeric impurity [15-22%; (2S,3R,5R)-3-methyl-7-oxo-3-(1H-1,2,3-triazol-1-ylmethyl)-4-thia-1-azabicyclo[3.2.0]heptane-2-carboxylic acid, 4,4-dioxide] was charged into methyl ethyl ketone (540 mL) under stirring at 28-30° C. The slurry obtained was warmed to 38-40° C. over a period of 20-30 min and maintained at this temperature for 60 min under efficient stirring. The slurry was filtered at 38-40° C. and suck-dried. The wet material was dried under vacuum at 25-30° C. over 5 h to get pure Tazobactam (26.02 g, purity >99.0%; isomeric impurity: 0.06%).

EXAMPLE 2

Purification of Tazobactam Using Acetic Acid

Tazobactam (35 g) containing the isomeric impurity [15-22%; (2S,3R,5R)-3-methyl-7-oxo-3-(1H-1,2,3-triazol-1-yl-methyl)-4-thia-1-azabicyclo[3.2.0]heptane-2-carboxylic acid, 4,4-dioxide] was charged into acetic acid (70 mL) at 25-30° C. under stirring. The mixture was cooled to 20-25° C. and maintained at this temperature for 30 min under vigorous stirring. The slurry was filtered and washed with purified water (50 mL) and suck-dried. The wet material was charged into a flask, containing methanol (50 mL) maintained at 0-2° C., stirred for 30 min and filtered. The wet material was unloaded and dried under vacuum at 25-30° C. for 6 h to get pure Tazobactam (23.65 g; purity: >99.0% & isomeric impurity: 0.06%).

EXAMPLE 3

Purification of Tazobactam Using Methyl Ethyl Ketone in the Presence of L-Tartaric Acid Tazobactam acid (50 g) containing the isomeric impurity [15-22%; (2S,3R,5R)-3-methyl-7-oxo-3-(1H-1,2,3-triazol-1-ylmethyl)-4-thia-1-azabicyclo[3.2.0]heptane-2-carboxylic acid, 4,4-dioxide] was charged into methyl ethyl ketone (350 mL) at 28-30° C. under stirring. To the slurry, L-tartaric acid (2.5 g) was added at 28-30° C. under efficient stirring. The temperature was raised to 35-38° C. over a period of 15-30 min and maintained under stirring at this temperature for 120 min. The heterogeneous solution was cooled to 28-30° C., maintained for 60 min and filtered. The wet material was unloaded and dried under vacuum to get pure tazobactam (38.0 g; purity: >99.0%), free of the isomeric impurity.

EXAMPLE 4

Preparation of Tazobactam from Penultimate Sulfone Ester

In to a 2 Lit hydrogenator, ethyl acetate (450 mL), wet sulfone ester [70 g, (2S,3S,5R)-3-methyl-7-oxo-3-(1H-1,2,3-triazol-1-ylmethyl)-4-thia-1-azabicyclo [3.2.0]heptane-2-carboxylic acid, 4,4,-dioxide, p-nitrobenzyl ester] containing the isomeric impurity (15-22%; (2S,3R,5R)-3-methyl-7-oxo-3-(1H-1,2,3-triazol-1-ylmethyl)-4-thia-1-azabicyclo[3.2.0] heptane-2-carboxylic acid, 4,4-dioxide, p-nitrobenzyl ester], purified water (160 mL), sodium bicarbonate (12 g) and Pd/C (10%, 10 g) were added and cooled to 15-20° C. The reaction mixture was hydrogenated at a pressure of 15-20 Kg/cm2 over 1 h and filtered. The filtrate was cooled to 10-15° C. and the organic layer separated. The aqueous layer was washed with ethyl acetate, and the pH of the aqueous layer was adjusted to 5.5. The aqueous layer was charcoalized at 10-15° C. To the filtrate, methyl ethyl ketone (150 mL) was added and the pH adjusted to 2.5 with conc. HCl. After maintaining for 20-30 min at 10-15° C., the pH was set to 1.2-1.3 with conc. HCl, maintained for 45 min and filtered. The crystallized product was washed with cold DM water and suck-dried. The wet material was dried under vacuum at 25-30° C. for 8 h to get pure tazobactam acid (25.0 g, purity: >99% and the isomeric impurity: 0.02%).

EXAMPLE 5

Purification of Sulfone Ester Using Methyl Ethyl Ketone in the Presence of Tartaric Acid To methyl ethyl ketone (250 mL), sulfone ester [25 g, (2S,3S,5R)-3-methyl-7-oxo-3-(1H-1,2,3-triazol-1-ylm-ethyl)-4-thia-1-azabicyclo[3.2.0]heptane-2-carboxylic acid, 4,4,-dioxide, p-nitrobenzyl ester] containing the isomeric impurity (15-22%; (2S,3R,5R)-3-methyl-7-oxo-3-(1H-1,2, 3-triazol-1-ylmethyl) -4-thia-1-azabicyclo[3.2.0]heptane-2-carboxylic acid, 4,4,-dioxide, p-nitrobenzyl ester] was added under stirring at 25-30° C. To the stirred mixture, L-tartaric acid (8.5 g) was added, warmed to 60-65° C. and maintained at this temperature for 90 min. The slurry was cooled to 30-35° C. in 45 min, maintained for 15 min and filtered and dried under vacuum for 4 h at 25-30° C. to afford the title compound in pure form (12.5 g; purity >99.0%).

EXAMPLE 6

Purification of Sulfone Ester Using Methyl Ethyl Ketone

To methyl ethyl ketone (100 mL), sulfone ester [10 g, (2S,3S,5R)-3-methyl-7-oxo-3-(1H-1,2,3-triazol-1-ylm-ethyl)-4-thia-1-azabicyclo[3.2.0]heptane-2-carboxylic acid, 4,4,-dioxide, p-nitrobenzyl ester] containing the isomeric impurity (15-22%; (2S,3R,5R)-3-methyl-7-oxo-3-(1H-1,2, 3-triazol-1-ylmethyl) -4-thia-1-azabicyclo[3.2.0]heptane-2-carboxylic acid, 4,4,-dioxide, p-nitrobenzyl ester] was added at 25-30° C. under stirring. To the stirred mixture, acetic acid (10 mL) was added at 25-30° C. and the slurry warmed to 65-70° C. for 15 min to get a clear solution. The clear solution was cooled to 28-30° C. over a period of 25 min, maintained for 30 min at 28-30° C. and filtered and dried under vacuum for 4 h to afford afforded pure title compound (5.0 g; purity: >98.0%).

EXAMPLE 7

Purification of Sulfone Ester Using DMSO in the Presence of Tartaric Acid

To dimethyl sulfoxide (40 mL), sulfone ester [10 g, (2S, 3S,5R)-3-methyl-7-oxo-3-(1H-1,2,3-triazol-1-ylmethyl)-4-thia-1-azabicyclo[3.2.0]heptane-2-carboxylic acid, 4,4,-dioxide, p-nitrobenzyl ester] containing the isomeric impurity (15-22%; (2S,3R,5R)-3-methyl-7-oxo-3-(1H-1,2,3-triazol-1-ylmethyl)-4-thia-1 -azabicyclo[3.2.0]heptane-2-carboxylic acid, 4,4,-dioxide, p-nitrobenzyl ester] was charged at 25-30° C. To the stirred reaction mixture, L-tartaric acid (3.4 g) was charged at 25-30° C. and maintained at this temperature for 30 min. Purified water (8 mL) was added, maintained under stirring for 4 h, filtered and washed with water and dried the product under vacuum for 8 h to afford the title compound (6.0 g; purity: >99.0%).

The invention claimed is:

1. An improved process for the preparation of tazobactam or its derivatives of the formula (I) having less than 0.5% w/w of impurity of formula (V)

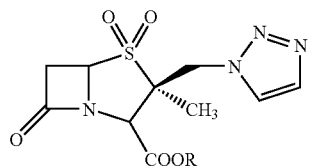

wherein R represents hydrogen,
which comprises the steps of:
  i) slurrying the compound of formula (I) containing the impurity of the formula (V)

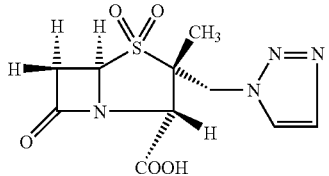

using a solvent selected from the group consisting of methyl ethyl ketone, acetic acid, formic acid, propionic acid, cyclohexanone and acetone, and optionally in the presence of tartaric acid and water, at 20-50° C., and
  ii) isolating the compound of formula (I) in a purity of 99% or more as measured by HPLC.

2. The process as claimed in claim 1, wherein tartaric acid is used in the form of L-tartaric acid, D-tartaric acid or (±)-tartaric acid.

* * * * *